(12) United States Patent
Redmond

(10) Patent No.: US 10,405,908 B2
(45) Date of Patent: Sep. 10, 2019

(54) APPARATUS AND METHOD FOR FORMING SUPPORT DEVICE FOR EFFECTING ORTHOPEDIC STABILIZATION

(71) Applicant: Warsaw Orthopedic, Inc., Warsaw, IN (US)

(72) Inventor: Jerald L. Redmond, Germantown, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 1006 days.

(21) Appl. No.: 14/574,595

(22) Filed: Dec. 18, 2014

(65) Prior Publication Data
US 2016/0175013 A1    Jun. 23, 2016

(51) Int. Cl.
B21D 7/14 (2006.01)
A61B 17/88 (2006.01)
B21D 7/12 (2006.01)

(52) U.S. Cl.
CPC ............ *A61B 17/8863* (2013.01); *B21D 7/14* (2013.01); *B21D 7/12* (2013.01)

(58) Field of Classification Search
CPC ... B21D 7/03; B21D 7/12; B21D 7/14; B21D 9/01; B21D 7/024; B21D 7/08; A61B 17/8863; A61B 17/72; A61B 5/0084; A61M 25/0009; G01B 5/20; G01B 5/201; G01B 5/241; G01B 11/24; G01B 11/2408
See application file for complete search history.

(56) References Cited

U.S. PATENT DOCUMENTS

| | | |
|---|---|---|
| 1,066,247 A | 7/1913 | Brown, Jr. |
| 1,514,467 A | 11/1924 | Schonfield et al. |
| 2,055,955 A | 9/1936 | Wagenbach |
| 2,502,713 A | 4/1950 | Fagge |
| 2,675,723 A | 4/1954 | Stein |
| 2,722,858 A | 11/1955 | Oyen |
| 3,657,914 A | 4/1972 | Hart |
| 3,908,425 A | 9/1975 | Ware |

(Continued)

OTHER PUBLICATIONS

Robin Young, Orthopedics This Week, The Ten Best New Spine Technologies of 2012, vol. 8, Issue 35, Nov. 6, 2012, www.ryortho.com.

(Continued)

*Primary Examiner* — Edward T Tolan

(57) ABSTRACT

A forming apparatus and method for forming a workpiece used a medical procedure is provided. A controllable bending machine for bending the workpiece is provided. A template is manually formable. The template has a shape sensor so as to sense a shape of the template. A controller receives template shape data from the shape sensor and operates the bending machine in accordance with the template shape data. The bending of the workpiece includes a spring back compensating operation which performs a first bending operation on the workpiece in accordance with the template shape data, acquires workpiece shape data from one of the shape sensor re-disposed associated with the workpiece, or another shape sensor associated with the workpiece, and performs a second bending operation compensating for spring back. A method employs the template for workpiece measurements and the forming apparatus using the measurements for forming the workpiece.

20 Claims, 9 Drawing Sheets

(56) References Cited

U.S. PATENT DOCUMENTS

| | | | |
|---|---|---|---|
| 4,292,834 A | 10/1981 | Tishler et al. | |
| 4,561,279 A | 12/1985 | Wears | |
| 4,788,847 A | 12/1988 | Sterghos | |
| 5,389,099 A | 2/1995 | Hartmeister et al. | |
| 5,901,600 A | 5/1999 | Decker | |
| 6,006,581 A | 12/1999 | Holmes | |
| 6,035,691 A | 3/2000 | Lin et al. | |
| 7,781,724 B2 | 8/2010 | Childers et al. | |
| 8,050,523 B2 | 11/2011 | Younge et al. | |
| 8,177,843 B2 * | 5/2012 | Schalliol | B21D 7/12 606/246 |
| 8,382,759 B2 * | 2/2013 | Tuma | A61B 90/36 606/329 |
| 8,434,337 B2 * | 5/2013 | Meitner | A61C 9/002 33/412 |
| 8,549,888 B2 | 10/2013 | Issacs | |
| 8,607,603 B2 * | 12/2013 | Justis | A61B 17/8863 140/123 |
| 8,773,650 B2 | 7/2014 | Froggatt et al. | |
| 9,072,556 B2 * | 7/2015 | Fritzinger | A61B 17/8057 |
| 9,485,473 B2 * | 11/2016 | Allen | H04N 7/18 |
| 9,636,181 B2 * | 5/2017 | Isaacs | A61B 17/7011 |
| 2003/0055435 A1 * | 3/2003 | Barrick | A61B 5/1077 606/102 |
| 2005/0262911 A1 | 12/2005 | Dankowicz et al. | |
| 2008/0285909 A1 | 11/2008 | Younge et al. | |
| 2013/0131499 A1 * | 5/2013 | Chan | A61B 8/0841 600/424 |
| 2014/0069187 A1 * | 3/2014 | Ranftl | G01K 13/02 73/431 |
| 2014/0180168 A1 * | 6/2014 | Millett | A61B 5/0084 600/587 |
| 2015/0320471 A1 * | 11/2015 | Crawford | B21D 7/12 72/11.1 |
| 2016/0001039 A1 * | 1/2016 | Armour | A61M 25/0009 72/342.92 |
| 2016/0228199 A1 * | 8/2016 | Flexman | G02B 23/2476 |
| 2017/0333968 A1 * | 11/2017 | Turanjanin | B21D 7/14 |
| 2017/0360493 A1 * | 12/2017 | Zucker | A61B 17/8863 |

OTHER PUBLICATIONS

David W. Wilson, Tip of the Month, Central Virginia Blacksmith Guild, Simple Bending Jig, Jun. 1998.

Scholarly Communication's About ETDs@VT, Electronic Theses and Dissertations at VT, Virginia Tech's Electronic Theses and Dissertations, Virginia Tech., Digital Library and Archives, URL: htttp://scholar.lib.vt.edu/theses/index.html Aug. 14, 2014.

Pilson, Richard Ryan; Master's Thesis, Master of Science, Title: Automated Manufacture of Spinal Instrumentation, Feb. 6, 2006.

* cited by examiner

APPARATUS AND METHOD FOR FORMING SUPPORT DEVICE FOR EFFECTING ORTHOPEDIC STABILIZATION

TECHNICAL FIELD

The present disclosure relates to methods and devices for forming a spinal rod for implantation with pedicle screws. More particularly, the present disclosure presents embodiments of methods and devices for effecting precise bending of spinal rods via manual and automated methods and devices.

BACKGROUND

Various procedures directed to remedying spinal disorders require that the vertebra of the spine be stabilized. Such procedures include spinal fusion. Pedicle screws are installed in pedicles of vertebra of a spinal portion to be fused. The pedicle screws include sockets for receiving and fixating a rod which is used to interconnect the vertebra in fixed relation to one another to stabilize the vertebra while healing takes place effecting fusion of the vertebra. Other medical procedures exist which require the implantation of formable metallic parts such as repair of broken bones requiring stabilization during the healing process.

In the case of first and second level spinal fusions, rods are typically provided pre-bent to a desired curvature required to restore the natural curvature of the spine. In cases of multi-level fusions, such as the correction of spinal deformities, rods are provided straight and bent by surgeons in the operating room to be custom configured to the needs of the patient. The bending is done manually using instruments such as a French bender or in-situ bending devices. The rods used are formed of stiff materials with high yield stress such as titanium alloys. For example, Ti-6A1-4V titanium has a yield stress of 110,000 psi. Hence, force applied to such material exceed the yield stress to effect permanent deformation of the material. Bending rods is a difficult procedure which is complicated by work hardening of the rods due to bending and elastic strain of the material which results in spring-back.

A bending machine for use in operating rooms has been proposed and implemented. See Richard Ryan Pilson, *Automated Manufacture of Spinal Instrumentation* (Feb. 6, 2006) (unpublished MSME thesis, Virginia Polytechnique Institute & State University) (on file with Virginia Tech's Electronic Theses and Dissertations http://scholar.lib.vt.edu/theses/available/etd-02192006-214714/) which is herein incorporated by reference. The bending machine incorporates feedback affected by a digital encoder which measures deflection both with bending pressure applied and after bending pressure is removed to determine spring back and subsequent bending angles to achieve a desired bend. Such a system measures one bend at a time by deflection of a feeler apparatus which makes contact with the rod to be bent and deflects with the rod to rotate a digital encoder which in turn provides a measurement of the deflection of the rod. Rods requiring multiple bends are formed with each bend being measured and data stored (local bend) so that a final rod shape may be determined by mathematically adding measured deflections along the rod to determine a final rod shape (global bend). This system is prone to cumulative errors in the successive bending process and does not provide a real-time measurement of the final rod contour as only one bend at a time can be measured. Hence, verification of the actual final contour of the rod cannot be made. The present disclosure describes an improvement over these prior art technologies.

SUMMARY

In some embodiments, a method and apparatus for forming components used in medical procedures which are fitted to a patient are provided. The apparatus allows accurate bending of components. In some embodiments, the apparatus and method permit accurate measurements to be taken in real-time and use of the measurements in controlling a bender to form the components.

In some embodiments, the apparatus and method of this disclosure allow a user to custom fit a workpiece to a patient, and digitize shape data representing the fitted workpiece. In some embodiments, the apparatus and method of this disclosure acquire digital measurements that represent shape data of a manually formed template representing a workpiece to be fitted to a patient.

In some embodiments, the apparatus and method of this disclosure form a workpiece based on shape data wherein spring back due to elastic strain is compensated. In some embodiments, the apparatus and method of this disclosure form a workpiece by bending the workpiece, which provides a real-time measurement of the workpiece shape and which compensates for spring back of the workpiece due to elastic strain.

In some embodiments, a forming apparatus and method for forming a workpiece used a medical procedure is provided. In some embodiments, a controllable bending machine for bending the workpiece is provided. In some embodiments, a template is manually formable. The template has a shape sensor to sense a shape of the template. In some embodiments, a controller receives template shape data from the shape sensor and operates the bending machine in accordance with the template shape data. In some embodiments, bending of the workpiece includes a spring back compensating operation which performs a first bending operation on the workpiece in accordance with the template shape data, acquires workpiece shape data from one of the shape sensor re-disposed associated with the workpiece or another shape sensor disposed associated with the workpiece, and performs a second bending operation compensating for spring back due to elastic deformation during the first bending operation. An embodiment of a method of this disclosure includes manually shaping the template and operating the bending machine via the controller to bend the workpiece in accordance with shape data obtained from the shape sensor included in the template.

In other embodiments of this disclosure, alternatives to using the optical shape sensor are provided using strain gauges, optical strain mapping, or optical curvature measurements. A bender optionally employs data representing material properties which are stored in a database, so that based on an expected yield stress of the material, the bender can over bend the first time so that the springback will be within the desired curvature tolerance. Such operation optionally uses either the stored material property data with or without pre-calibration, or real-time stiffness measurements of the force displacement curve to detect the elastic/plastic transition for determining the amount of additional overbend needed to achieve a desired springback.

In one embodiment of this disclosure, a method comprises providing the forming apparatus of any of the above embodiments, manually shaping the template to fit the patient, and operating the controller to effect bending of the workpiece by the bender based on the template shape data and the workpiece shape data using the spring back compensating operation. The method optionally includes manually forming the template in-situ by placing the template in position where the workpiece is installed while forming the template to conform to the required in-situ configuration of the workpiece.

BRIEF DESCRIPTION OF THE DRAWINGS

In part, other aspects, features, benefits and advantages of the embodiments will be apparent with regard to the following description, appended claims and accompanying drawings where:

Figure 1:
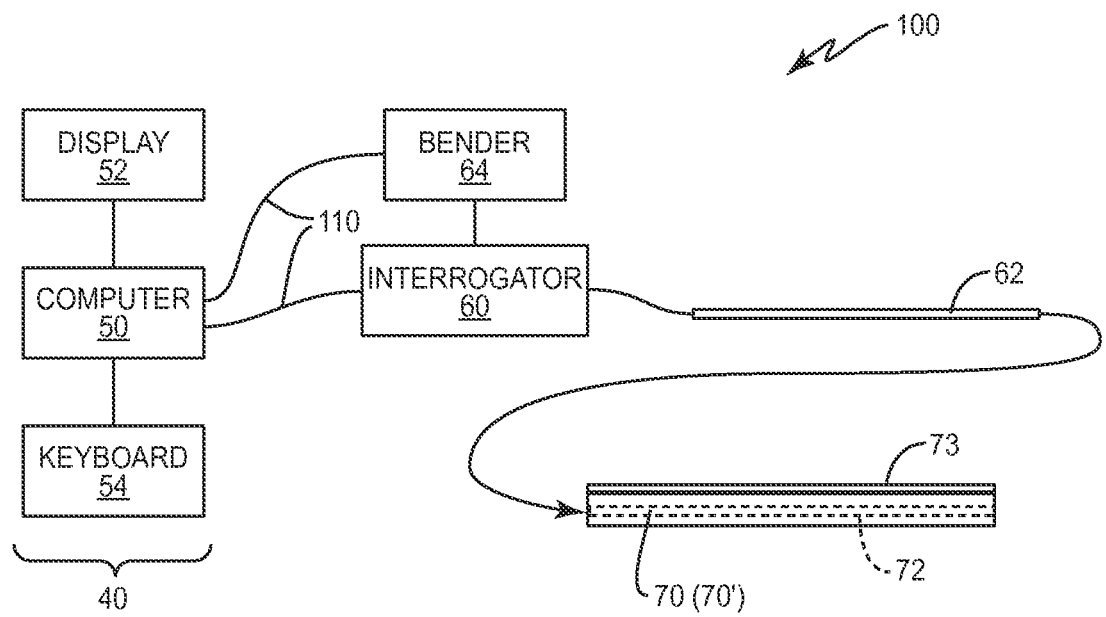
FIG. 1 is a schematic of an embodiment of a bending apparatus of the present disclosure.

It is to be understood that the figures are not drawn to scale. Further, the relation between objects in a figure may not be to scale, and may in fact have a reverse relationship as to size. The figures are intended to bring understanding and clarity to the structure of each object shown, and thus, some features may be exaggerated in order to illustrate a specific feature of a structure.

DETAILED DESCRIPTION

For the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the embodiments of the present disclosure. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to disclose and encompass any and all subranges subsumed therein. For example, a range of "1 to 10" includes any and all subranges between (and including) the minimum value of 1 and the maximum value of 10, that is, any and all subranges having a minimum value of equal to or greater than 1 and a maximum value of equal to or less than 10, e.g., 5.5 to 10.

It is noted that, in some embodiments, as used in this specification and the appended claims, the singular forms "a," "an," and "the," include plural referents unless expressly and unequivocally limited to one referent. Thus, for example, reference to "a bend" includes one, two, three or more bends.

Reference will now be made in detail to various embodiments of the present disclosure, examples of which are illustrated in the accompanying drawings. While the embodiments of the present disclosure will be described in conjunction with the illustrated embodiments, it will be understood that they are not intended to limit the disclosure to those embodiments. On the contrary, the disclosure is intended to cover all alternatives, modifications, and equivalents, which may be included within the disclosure as defined by the appended claims.

The headings below are not meant to limit the disclosure in any way; embodiments under any one heading may be used in conjunction with embodiments under any other heading.

The present disclosure provides an embodiment of a forming apparatus, wherein the template has the shape sensor optionally disposed in a channel which is one of a groove or a bore, and the workpiece has either the shape sensor of the template re-disposed associated with the workpiece or another shape sensor disposed with the workpiece, wherein the shape sensor is optionally placed in a channel which is one of a groove or a bore in the workpiece.

In one embodiment of the present disclosure, there is provided a template which optionally includes a sleeve and the shape sensor is disposed in the sleeve, and the workpiece has either the shape sensor used with the template re-disposed associated with the workpiece or another shape sensor disposed associated with the workpiece optionally retained in one of the sleeve or another sleeve.

In another embodiment detailed herein there is provided a forming apparatus according to any of the above embodiments wherein the controller is configured to accept linear identifier coordinates identifying target positions along the template, the template includes indicia identifying linear positions along the template, and the controller is configured to effect minimum bend bending via the bender wherein a number of bends, between the target positions, is minimized and bends are effected outside of defined areas including the target positions. In a further variation of this embodiment the controller is optionally configured to accept linear identifier coordinates identifying the defined areas.

In another embodiment detailed herein there is provided a forming apparatus according to any of the above embodiments wherein the template optionally includes a linear touch sensor for accepting contact at a position to effect input of coordinates of the position of the contact, the controller is configured to accept input from the linear touch sensor as linear identifier coordinates identifying target positions along the template, and the controller is configured to effect minimum bend bending via the bender wherein a number of bends, between the target positions, is minimized and bends are effected outside of defined areas including the target positions. In an optional variation of this embodiment the controller is configured to accept input from the linear touch sensor as linear identifier coordinates identifying the defined areas.

In another embodiment of this disclosure, a method comprises providing the forming apparatus of any of the above embodiments, manually shaping the template to fit the patient by placing the template in-situ while manually forming the workpiece to a configuration dictated by the in-situ placement of the template, and operating the controller to effect bending of the workpiece based on the template shape data and the workpiece shape data using the spring back compensating operation. In an optional variation of this method the template is limp and the manually forming comprises laying the template in-situ and acquiring the template shape data with the template laying in-situ.

In yet another embodiment of this disclosure, a method comprises providing the forming apparatus of any of the above embodiments having a linear touch sensor, manually shaping the template to fit the patient, inputting linear identifier coordinates of at least one of the target positions or the defined areas by touching the linear touch sensor, and operating the controller to effect the minimum bend bending of the workpiece based on the template shape data, the workpiece shape data, and the linear identifier coordinates of at least one of the target positions or the defined areas, using the spring back compensating operation. In an optional variation of this embodiment, the manual shaping of the template includes manually forming the template to fit the patient by placing the template in-situ while manually forming the template to a configuration dictated by the in-situ placement of the template. In a variation of this embodiment, the template is optionally limp and the manually forming comprises laying the template in-situ and acquiring the template shape data with the template laying in-situ.

In any of the above embodiments, the workpiece is optionally a spinal rod, the shape sensor optionally includes a fiber optic shape sensor, and the other shape sensor, if present, is optionally a fiber optic shape sensor.

Referring to FIG. 1, an embodiment of a bending apparatus 100 of the present disclosure includes a controller 40 which is shown optionally implemented by a computer 50 having a display 52 and a keyboard 54. Alternatively, a dedicated controller may be employed which incorporates a display and input controls. An interrogator 60 is connected to the controller 40 and interfaces with a fiber optic shape sensor 62. The fiber optic shape sensor 62 is a device comprised of optical fiber cores which, when connected to the interrogator 60, has a laser signal applied thereto and reflections from the laser signal analyzed by the interrogator 60 using optical frequency domain reflectometry (OFDR) to determine a shape imposed on the fiber optic shape sensor 62. The depiction of the interrogator 60 and fiber optic shape sensor 62 is simplified for purposes of clarity and may include additional components, such as a measurement interferometer head and a laser source, interfacing the fiber optic shape sensor 62 with the interrogator 60. One such system is available from Luna Innovations Incorporated, 1 Riverside Circle, Suite 400, Roanoke, VA 24016. Press Release, Luna Innovations Inc., see *Fiber Optic Shape Sensing—Current State of Technology* (Jun. 21, 2013), published by Luna Innovations Incorporated and herein incorporated by reference for teaching implementing fiber optic shape sensing. An embodiment of a fiber optic shape sensor is disclosed in U.S. Pat. No. 8,773,650, issued Jul. 8, 2014, which is incorporated herein by reference for its enabling disclosure of a fiber optic shape sensor. This disclosure is not limited to use of a fiber optic shape sensor employing OFDR but may incorporate other shape sensing technologies which provide functionally similar results. Hence, the term "shape sensor" as used herein is intended to mean any device which can be positioned in a configuration and provide data representing the configuration. In the embodiment depicted, the fiber optic shape sensor 62 is inserted into a sensor channel 72 in a workpiece, for example a spinal rod 70 which is to be formed to a desired configuration.

The controller 40 effects control of various components of the bending apparatus 100 via a signal transmission system 110 shown as the interconnection of components of the bending apparatus 100 to the controller 40. The signal transmission system 110 may take the form of any type of interconnection arrangement suitable to interface the components of the bending apparatus 40. For example, the signal transmission system 110 may comprise a NI UMI 7764, IEEE-488 (GPIB), RS-232, RS-485, USB, FireWire or Ethernet interconnection, or any combination thereof as necessitated by interfaces provided on the components of the bending apparatus 100. Furthermore, the signal transmission system 110 may also comprise individual control lines for driving components of the bending apparatus 100 that are solenoid or motor actuated. Still further, the signal transmission system 110 may also comprise signal carrying lines for carrying analog signals to and/or from sensors. The particular type of interconnection used for a given component will be determined by the interface provided on the component. Still further, although the signal transmission system 110 is shown physically interconnecting the controller 40 with the components of the bending apparatus 100 for purposes of clarity, this physical interconnection is not limiting insofar as the signal transmission system 110 may be effected wirelessly via optical (infrared for example) or RF means.

In alternative embodiments the controller 40, may optionally include a laptop, notebook, or tablet configuration wherein the display 52 and the computer 50 are integrated together. Furthermore, in the case of a tablet configurations, the keyboard 54 may be omitted and replaced by on-screen touch keyboards (not shown) or other input devices which are functional as keyboard or mouse replacements. Still further, another alternative embodiment of the controller 40 incorporates either, or both of the bender 64 and interrogator 60 to result in a unit which effects the bending and has a connection for the shape sensor 62.

Figure 2:
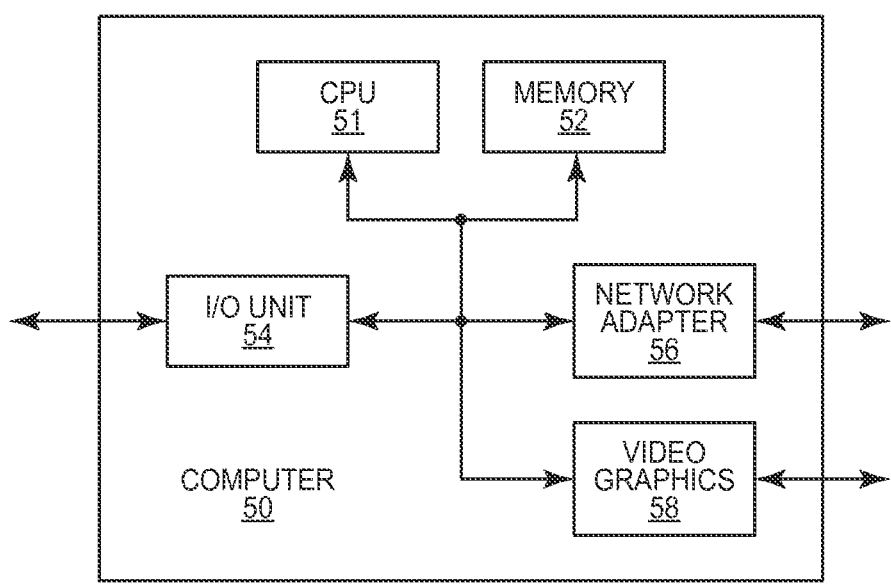
FIG. 2 is a block diagram of an embodiment of a computer of the bending apparatus of FIG. 1.

Referring to FIG. 2, an embodiment of an exemplary configuration of the computer 50 is shown. The exemplary embodiment of the computer 50 shown includes a central processing unit (CPU) 51, a memory 52, an input output (I/O) unit 54, a network adapter 56, and a video graphics adapter 58. The memory 52 is implemented by any one of a or combination of hard disk, RAM, or ROM. The I/O unit 54 implements communication with local devices such as the keyboard 33, the mouse 34, and the pen input device 60 via a USB or other known transmission standards. The network adaptor 56 implements communication over local area networks (LAN) such as those effected by a USB, FireWire or Ethernet interconnection. Those skilled in the art will appreciate in light of the present disclosure that the aforesaid components need not be independently embodied but may be integrated together as required for or permitted by a given application.

Figure 3A:
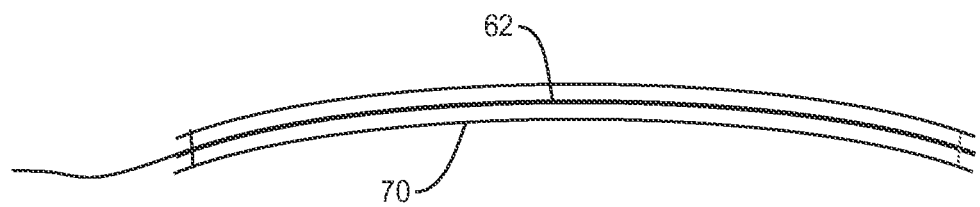
FIG. 3a is a side elevation view of a first embodiment of a workpiece having a fiber optic shape sensor disposed in a channel.

Referring to FIG. 3a, the fiber optic shape sensor 62 is disposed into the sensor channel 72. The sensor channel 72 is optionally a cylindrical bore dimensioned to receive the fiber optic shape sensor 62 with sufficient clearance so as not to exert compressive force on the fiber optic shape sensor 62 when the spinal rod 70 is formed to a final desired shape as a result of narrowing the sensor channel 72 due to bending the spinal rod 70. The fiber optic shape sensor 62 is used to detect a shape of the spinal rod 70 by virtue of the bending of the fiber optic shape sensor 62 causing refractive changes in the fiber optic shape sensor 62 which is caused by strain in optical fibers of the fiber optic shape sensor 62. Hence, for accurate measurements, it is important that bending of the spinal rod 70 not result in narrowing the sensor channel 72 to a point where walls of the sensor channel 72 pinch the fiber optic shape sensor 62. As an optional alternative to a cylindrical bore, other bore shapes such as oval, square, triangular, or other arbitrary shapes maybe used which may or may not have a configuration dictated by the fiber optic shape sensor 72. Still further, in place of a bore, the sensor channel is optionally configured as a groove formed in the spinal rod 70 which is configured to accept the fiber optic shape sensor 62.

Figure 3B:
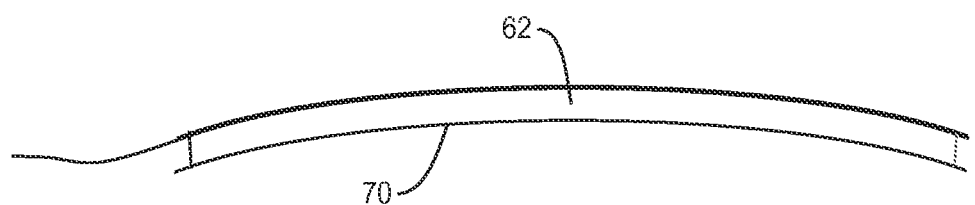
FIG. 3b is a side elevation view of a second embodiment of a workpiece having a fiber optic shape sensor disposed on a surface.

Referring to FIG. 3b, an alternative arrangement for sensing shape of the spinal rod 70 is one wherein the fiber optic shape sensor 62 is adhered to a surface of the spinal rod 70. Adherence may optionally be achieved by tape, tacky adhesive permitting removal, or more permanent adhesives or fastening techniques. Still further, the fiber optic shape sensor 62 may be incorporated into a sleeve which fits over the spinal rod 70. The sleeve is optionally elastic to allow expansion sufficient to allow the sleeve to contour to the form of the template, i.e., the spinal rod 70 is this example. Such arrangements allow use of a surgical rod which is not specially configured with a sensor channel 72 in the form of a bore or a groove. While this arrangement eliminates the possibility of compressive force on the fiber optic shape sensor 62 due to narrowing of the sensor channel 72, care must be taken to ensure that the fiber optic shape sensor 62 is not positioned on the spinal rod 70 where the bender 64 will exert pressure to bend the spinal rod 70. Such an arrangement is adequate when the bending will be substantially in one plane or only in planes that do not include the fiber optic shape sensor 62.

Figure 4A:
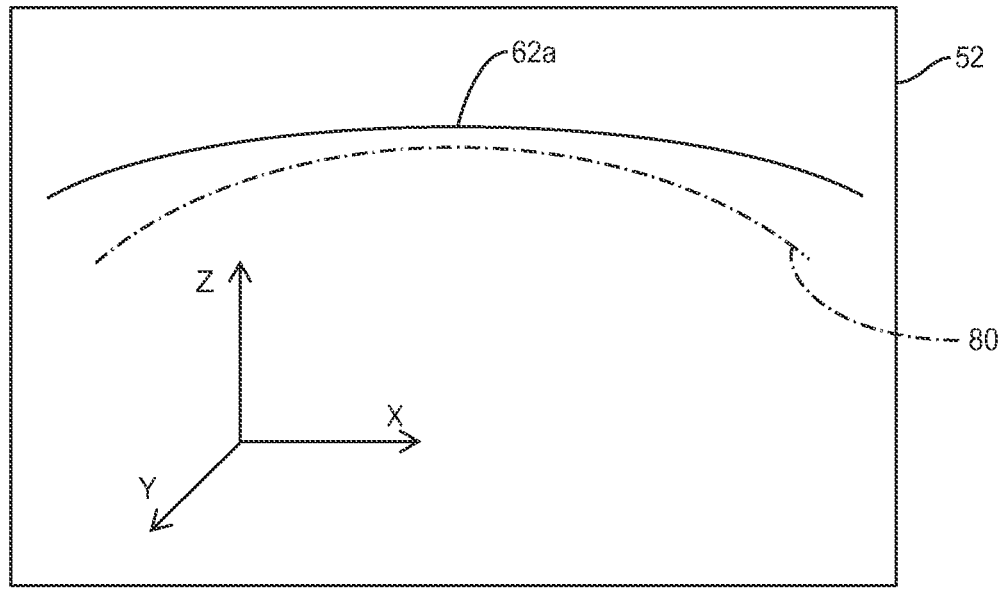
FIG. 4a is a depiction of a first embodiment of a screen display of the bending apparatus.

Referring to FIG. 4a, application software stored in the memory 52 receives input from the fiber optic shape sensor 62 and produces a real-time display of the spinal rod shape on the display 52 in the form of a sensor image line 62a which reflects the shape of the fiber optic shape sensor 62. Concurrently, the application software produces a target line 80 which represents the final desired configuration if the spinal rod 70. Thus, when the spinal rod 70 is bent, the shape of the spinal rod 70 is reflected on the display 52 and progression of the bending toward the target line 80 can be observed. Using the controller 40, the fiber optic shape sensor 62 and the interrogator 60, the bender 62 is operated to automatically bend the spinal rod 70 to a desired shape. Alternatively, a surgeon can manually bend the rod to a desired shape by observing the display 52.

Figure 4B:
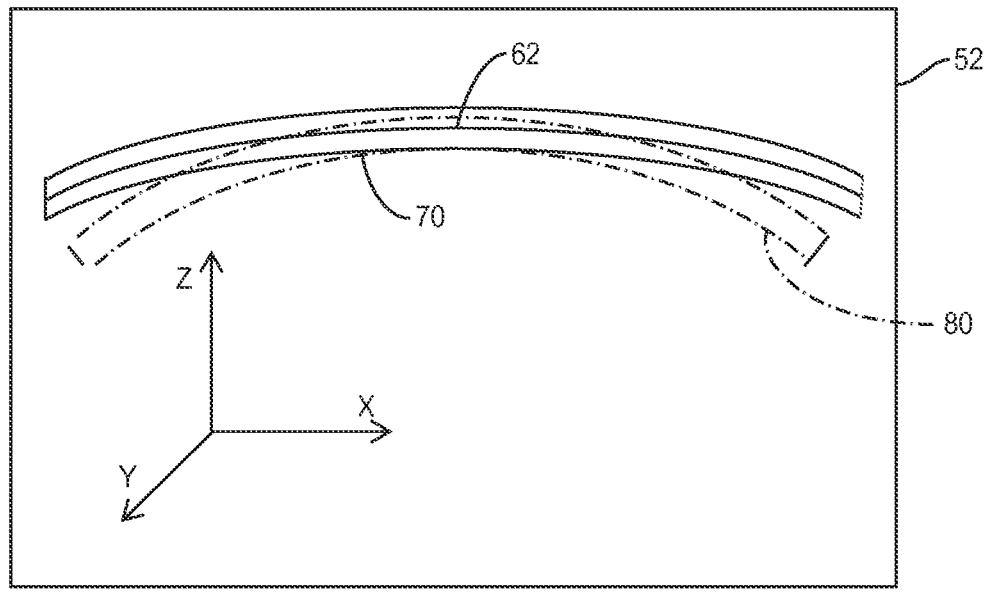
FIG. 4b is a depiction of a second embodiment of a screen display of the bending apparatus.

The display 52 presents a planar image which can be reoriented via input from the keyboard 54 or other device, such as a mouse or track ball, so that bends in other planes may be observed. Furthermore, an optional embodiment includes use of a 3D display which further aids in forming the spinal rod 70. Referring to FIG. 4b, another embodiment of the rod shape display includes depiction of the rod shape outline superimposed upon a target rod shape outline. Such a depiction can further assist the surgeon in visualizing the rod shape and manipulations required to achieve the desired rod shape. Other optional embodiments of the real-time rod shape display can include simultaneous display of multiple views from two or more perspectives which allow visualization of the 3D shape of the spinal rod 70. Still further, in the case where the fiber optic shape sensor 62 is adhered on a surface of the spinal rod 70, as in FIG. 3b, an offset can be introduced to produce a display indicative of a center axis of the spinal rod 70.

In spinal surgery for fusing vertebrate, pedicle screws are installed in the vertebra to be stabilized. It is realized that the present bending apparatus 100 is suitable for other medical uses, besides spinal stabilization, which require forming members to custom shapes dictated by the application. While ideally each pedicle screw is installed in the same orientation in each vertebra, this is not the case in practice. The pedicle screws may vary in insertion position, insertion angle, and insertion depth from vertebra to vertebra. In the vertebra fusing procedure, the spinal rod is attached to engagement configurations in heads of the pedicle screws to effect stabilization of the vertebra relative to one another. Since the actual installation of the pedicle screws is not ideal, the spinal rod can be configured to account for variations from the ideal installation of the pedicle screw. Thus, ideally, a determination of the required shape of the spinal rod 70 is made once the pedicle screws are installed so that the desired shape of the spinal rod 70 may compensate for variations from ideal installations of pedicle screws.

To determine the desired shape of the spinal rod 70, a template 70' is optionally used which incorporates the fiber optic shape sensor 62. In one example of this disclosure, the template 70' is a rod which has a same configuration as the spinal rod 70 and incorporates the fiber optic shape sensor 62 in the same manner as the spinal rod 70. The template 70' will have a configuration functionally corresponding to the actual spinal rod 70 but formed of a malleable material such as soft metals, e.g., soft copper, or manually formable plastics, rubber, or silicone materials. An embodiment of a template 70' has a soft malleable body, such as soft rubber or silicone material, which includes a ductile metal insert, for example, soft copper, or aluminum wire, embedded in the rubber so that a formed shaped may be retained, yet require little force to effect formation. Such a construction might employ copper wire ranging from 12 to 18 AWG. In the particular example of a spinal rod 70, the template rod will have a diameter in the range of 8.5 to 10 mm which is typical of spinal rods used for spinal fusion procedures. From a structural characteristic standpoint, one embodiment of the template 70' optionally has a sufficient yield strength to be self-supporting when supported at an end without undergoing plastic deformation due to its own weight. This allows the template 70' to be moved and handled without disturbing a shape to which the template 70' has been formed. However, to facilitate manual shaping, the template, e.g., the template 70' preferably has a bending moment yield strength $M_y$, preferably in the range of 1 lb-ft to 0.05 lb-ft, more preferably in the range 0.5 lb-ft to 0.05 lb-ft, and still more preferably in the range 0.25 lb-ft to 0.1 lb-ft. For purposes of this disclosure, "manually formable" is intended to mean a material which may be manually formed by hand without need of leveraging aids or has a bending moment yield strength equal to or less than 1 lb-ft.

Another embodiment of a manually formable template includes a link construction wherein the links are joined so as to exhibit a friction force or mechanical force applying construction, such as a biased detent configuration, which restricts relative movement of links without manual manipulation. Such a link construction is optionally metallic, or other material which will allows sterilization. Yet another construction of the template 70' optionally includes spiral wound plastic or metallic member similar to that used in flexible gooseneck lamps and BX armored cable which is manually formable. Such construction allows use of metallic material, such as stainless steel for example, which facilitate sterilization.

Generally, a template will typically be dimensioned to represent the size and shape of a member to be formed by the bender 64, however, this is not required and the present disclosure includes templates which do not mimic the overall size and shape of the part to be formed. For example, in some situations only certain portions of a template need be positioned to produce configuration data with other portions of the template, in between, the certain portions being irrelevant in the given application. Hence, as used herein, the term "functionally conforming" with regard to form means a shape sufficient to permit shaping of a template to produce measurements necessary to shape a workpiece to meet functional requirements. In the case of the spinal rod 70, the template 70' need not have the same diameter throughout as the spinal rod 70, but need only have areas which are to engage the pedicle screws matching the form of the spinal rod 70. These are the areas which function to engage the pedicle screws hence the form of these areas should match the form of the actual workpiece, in this example, the spinal rod 70. Other areas of the template 70' may be of smaller diameter and differing contour since these areas of the spinal rod 70 do not physically engage other components.

The template of this disclosure is not limited to the above dimensions and strength characteristics. For example, applications may require that a template be flaccid or limp such that the template may conform to a surface upon which it is disposed under its own weight so that a contour of the surface can be determined without applying force to the template to conform to the surface. Such a template is useful where manual shaping of the template is not required and the surface upon which the template is disposed dictates a shape of a part to be formed by the bender 64.

The surgeon can easily manually form the template 70', with the fiber optic shape sensor 62 installed in the template 70', to a shape dictated by the actual positions of the pedicle screws while in the operating room. The template 70' is optionally situated to engage the installed pedicle screws in-situ, in the same manner as the actual spinal rod 70, to verify the correct shape without actual installation of the spinal rod 70. The fiber optic shape sensor 62 is then polled by the interrogator 60 and its shape digitized. Once the template rod is finally shaped, the application software stores the digitized desired shape sensed by the fiber optic shape sensor 62.

Alternatively, a desired shape of the spinal rod may be determined from digital images of an in-situ 3D scan, or in-situ x-rays of the patient with the pedicle screws installed. Still further, 3D optical scanning of the patient may be effected to produce a digitized image of relative positioning of the engagement configurations of the pedicle screws. Yet another option is to employ a sensing device other than the template 70' which makes contact with installed pedicle screws to ascertain a desired shape of the spinal rod and digitize and store the shape. One such device employs individual articulated arms to respectively engage the pedicle screws and which are equipped with digital encoders to permit digitization of relative positions of the engagement configurations of the pedicle screws. See *Automated Pedicle Screw Rod Bender*, U.S. Pat. No. 8,177,843, which is herein incorporated by reference.

When digitized positions of the engagement configurations of the pedicle screws are obtained, a curve fitting procedure is optionally used to interconnect the positions of the engagement configurations thus determining the desired shape of the spinal rod 70. Other methods are optionally used to determine the final shape of the rod which will take into account bending characteristics of the bender 64 and material of the spinal rod 70.

It is a further feature of this disclosure that following production of digital desired shape data based on the digitized positions of the engagement configuration, an actual spinal rod 70 is loaded into the bender 64 and formed by the bender 64 into the desired shape in accordance with the digital desired shape data. Various bending methods may be employed to achieve the desired shape. Bends in the spinal rod 70 may be made at a series of incremental positions to produce a piecewise linear approximation of the desired shape. Alternatively, the bender 64 may be operated to produce continuous bends by axially advancing the spinal rod 70 through a bending member and mandrel to simultaneously effect bending of the rod. This is a more complex operation and may not be needed in applications such as spinal fusion wherein only the positioning of points, or areas, along the spinal rod 70 that engage the pedicle screws are relevant. However, such continuous bending is optionally employed and is considered advantageous in applications wherein the overall contours of a rod is of importance to achieve either cosmetic or functional objectives.

Figure 5:
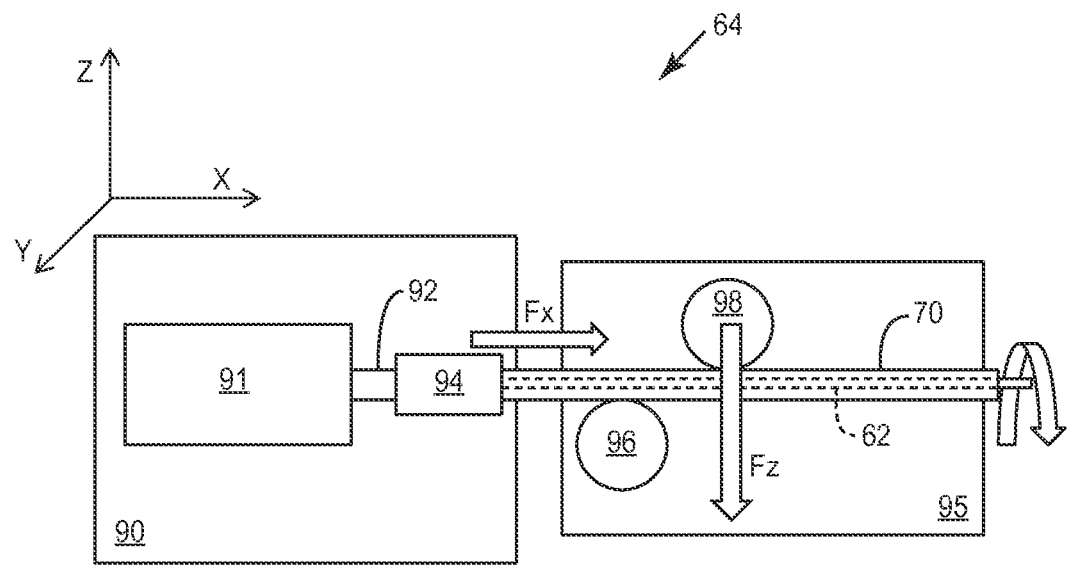
FIG. 5 is a schematic of an embodiment of a bender of the bending apparatus.

Referring to FIG. 5, a schematic diagram of an embodiment of the bender 62 illustrates an arrangement of a bending configuration. A rod support assembly 90 includes a stepper motor 91 having a collet 94 mounted on an output shaft 92. The collet 94 is configured to receive and clamp the spinal rod 70. The collet 94 may be alternatively embodied as a chuck or other clamping device for securing the spinal rod 70 to the shaft 92. The stepper motor 91 serves to rotate the spinal rod 70 in a bending assembly 95 to effect bends in differing radial planes of the spinal rod 70. The bending assembly 95 has a mandrel member 96 and a bending member 98 which may be embodied as rotatably or non-rotatably mounted cylinders or other shape configurations as may be dictated by a workpiece. The rod support assembly 90 and the bending assembly 92 are supported to be movable relative one another in the x-axis direction. The mandrel member 96 is mounted in the bending assembly to be fixed in position relative to the shaft axis of the output shaft 92 and an axis of the spinal rod 70. Although fixed during a bending operation, the mandrel member 96 is optionally movably mounted relative to the spinal rod axis to accommodate spinal rods of differing diameters or a spinal rod having a varying diameter along its length. The bending member 98 is movably supported in the bending assembly to effect motion at least in part in the z-axis direction relative to the spinal rod axis to engage the spinal rod 70 and exert a force Fz sufficient to effect permanent deformation of the spinal rod 70 about the mandrel member 96.

Rotation of the stepper motor 91, actuation of an x-axis drive mechanism for the relative motion of the rod support assembly 90 and the bending assembly 95, and actuation of the bending member 98 at least in part in the direction Fz relative the spinal rod axis are directed by the computer 50 based on the digital desired shape data. Although not shown for purposes of clarity, it is understood that the bender 64 optionally includes a bender controller or controllers for directing actuation of the stepper motor 92, and motors (not shown) driving the bending member 98 and effecting relative motion of the rod support assembly 90 and the rod bending assembly 95. The bender controller optionally accepts high level commands dictating operation of the bender 64 and handles the tasks of actual motor control via motor drive circuits. Alternatively, control is optionally accomplished by the computer 50 directly controlling motor drive circuits. Various divisions of control functions may be employed within the scope and spirit of the present disclosure.

It is understood that the movement of the bending member 98 may be linear, arcuate, or an arbitrary path so long as bending of the spinal rod 70 is achieved. It is to be further understood that the illustrated embodiment of the bender 64 is exemplary and various alterations may be made as are known to those skilled in the art of manufacturing equipment design, and in particular wire or pipe forming equipment. It will be further understood that for applications requiring bending in only one plane, continuously varying an angle of rotation of the stepper motor 91 is not required and any mechanism capable of effecting rod bending in both directions of a plane, i.e., effecting 180 degree relative rotation the spinal rod 70 and the bending assembly 95, may be employed.

Figure 6:
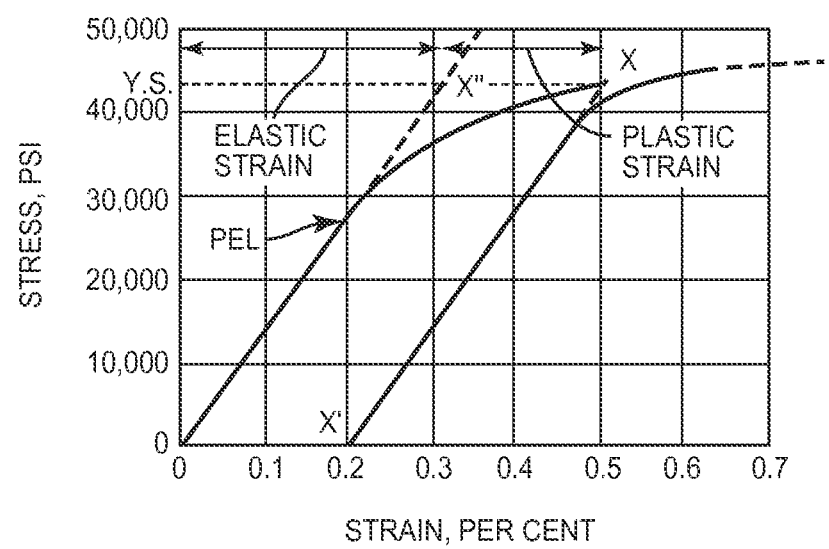
FIG. 6 is an exemplary graph of a stress-strain characteristic of a metal material showing elastic strain and plastic strain curve portion of the characteristic of the metal material of a workpiece.

Referring to FIG. 6, the bending of materials to a desired final configuration requires that the material be subjected to both elastic and plastic strain which results in permanent deformation (permanent set) of the material to the desired configuration. This process is complicated by the existence of spring back due to elasticity of the material which results in the material not maintaining a bend but instead partially returning to an original configuration. As shown in FIG. 6, material subjected to stress first undergoes elastic strain and then plastic strain following along the stress strain curve 0-X. Upon removal of stress, the material will spring back an amount equal to the elastic strain along the curve X-X'. The final plastic deformation is the amount 0-X'. Thus, in the illustrated graph a material must be subjected to 0.5% strain to produce 0.2% permanent deformation. Thus, the spinal rod 70 must be bent further than a desired bend angle to achieve a permanent set equal to the desired bend angle. Hence, the process of bending the spinal rod 70 can account for spring back.

The transition between elastic strain and plastic strain is not always well defined and the plastic strain characteristic is a complicated function which presents difficulty in accurately predicting plastic strain and the resultant permanent set which limits use of open loop bending (bending without feedback for effecting correction for spring back) to very well defined repeatable operations such as mass production of identical parts. This is clearly not the case when contouring support members for medical applications, such as spinal rods, wherein each case is substantially unique. Furthermore, once a material experiences plastic strain it undergoes work hardening which changes the stress strain characteristic of the material as illustrated in FIG. 6 wherein a subsequent bend of the material follows the curve from X' linearly until it again deviates from linear and follows the curve extending further to the right in FIG. 6. The characteristic presented in FIG. 6 is for exemplary purposes only and is not intended to limit this disclosure or be quantitatively accurate for materials used in spinal rods.

Figure 7:
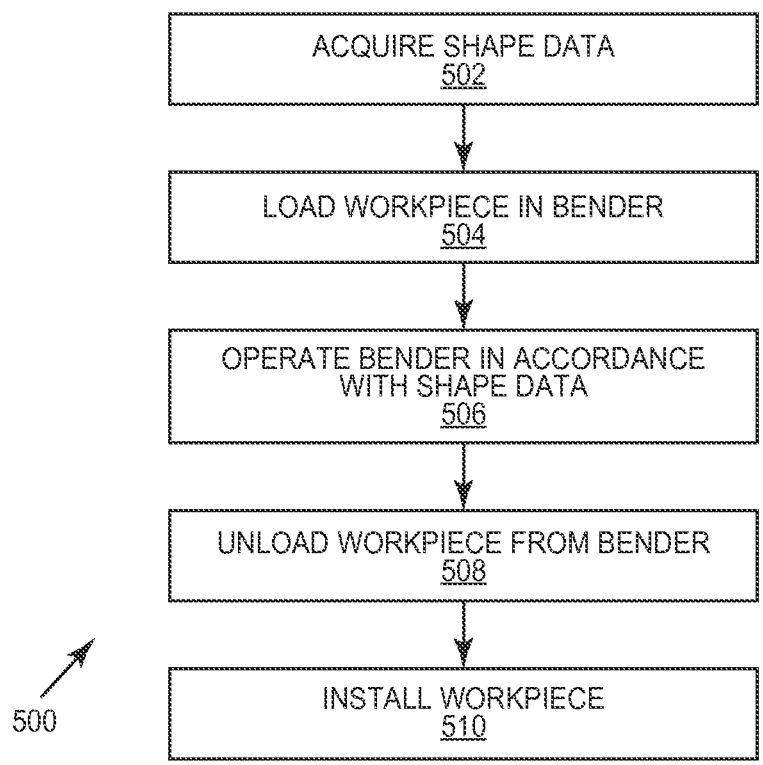
FIG. 7 is a flowchart of a forming method for forming and installing a workpiece.

The present disclosure provides a method for effecting accurate formation of support members prepared for unique situations particularly, but not exclusively, in the medical field, such as spinal rods for spinal fusion. Referring to FIG. 7, a generalized forming method 500 includes a data acquisition operation 502 for acquiring shape data. This operation is optionally conducted in accordance with any of alternative embodiments discussed below. A loading operation 504 is performed wherein the workpiece, for example a spinal rod blank, is mounted into the bender 64 by clamping the workpiece in the collet 94, chuck, mandrel, or other type of fixation apparatus for connecting the workpiece to the support assembly 90. Next, a forming operation 506 is performed wherein the bender 64 is operated using the shape data to form the workpiece. The forming operation 506 may be conducted in accordance with any of the alternative embodiments of the operation discussed below or other functionally equivalent embodiments. Following formation of the workpiece, an unloading operation 508 removes the workpiece from the bender 64 and then an installation procedure is conducted, for example by a surgeon, when the workpiece is a spinal rod.

Figure 8A:
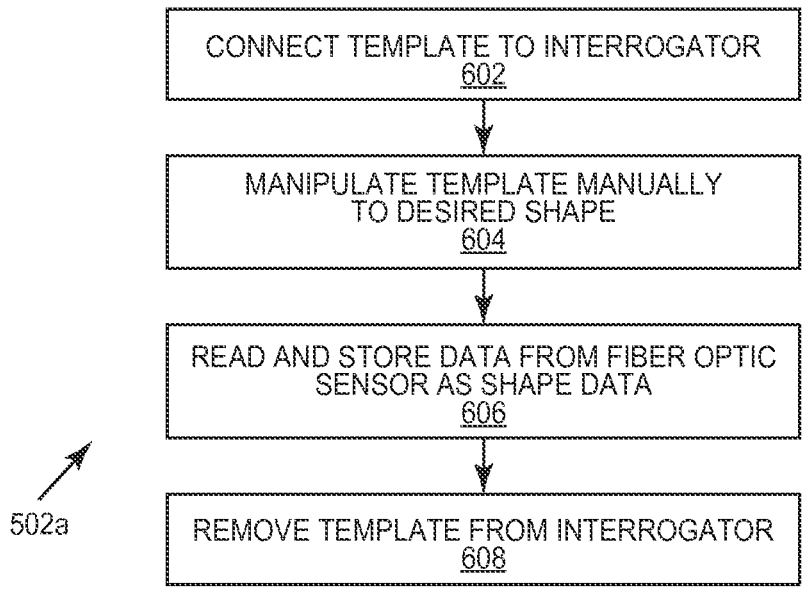
FIG. 8a is a flowchart of a first embodiment of a data acquisition operation of the forming method of FIG. 7 entailing manipulation of a template.

Referring to FIG. 8a, the data acquisition operation 502 is optionally embodied as first data acquisition operation 502a. A mounting operation 602 comprises connecting the template 70' to the interrogator 60. Next a shaping operation 604 comprises manually manipulating the template 70' to a desired shape. In the case of spinal fusion, the surgeon forms the template 70' by hand to the desired shape for connection to the pedicle screws while observing a template fit to pedicle screws installed in a patient. In an exemplary application of this method to spinal fusion, this process optionally includes forming the template 70', placing it on the pedicle screws, observing the fit, and then further forming the template 70', if necessary, and again placing it on the pedicle screw to observe the fit. This process is repeated until the surgeon is satisfied with the manually formed template 70'. A data storing operation 606 is then conducted wherein the interrogator 60 is polled for shape data of the template 70' and the shape data is stored in the controller 40. The template 70' is then removed from the interrogator 60 in operation 608.

Figure 8B:
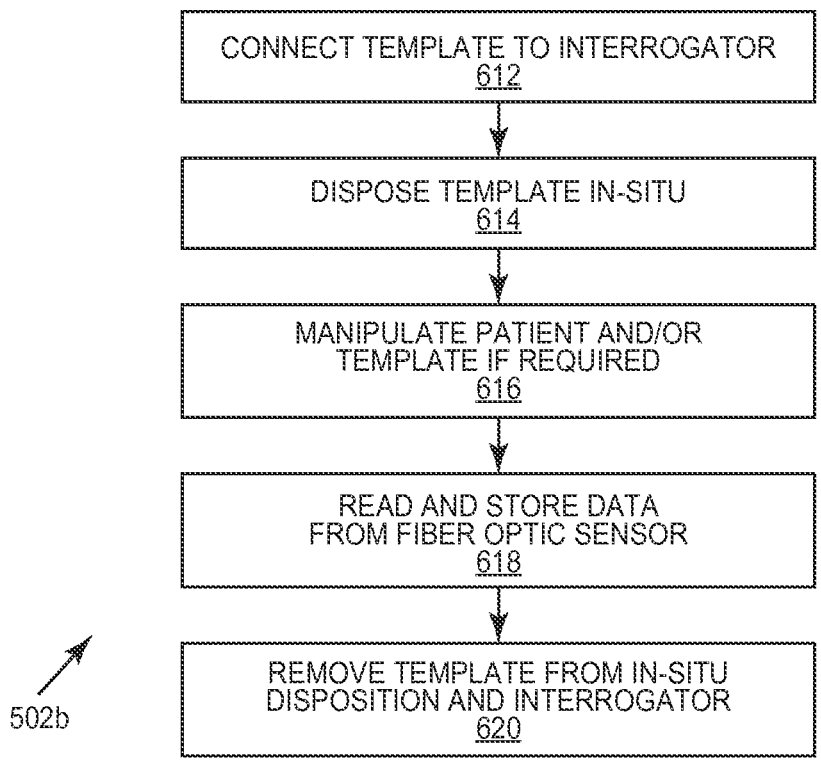
FIG. 8b is a flowchart of a second embodiment of a data acquisition operation of the forming method of FIG. 7 entailing in-situ disposition of the template.

Referring to FIG. 8b, the data acquisition operation 502 is optionally embodied as a second data acquisition operation 502b. The second embodiment of the data acquisition operation 502b includes a mounting operation 612 connecting the template 70' to the interrogator 60. The template 70' is then positioned on the pedicle screws in the disposition operation 614. In the case of spinal fusion, the surgeon disposes the template 70' in-situ, i.e., on the pedicle screws in the manner the actual spinal rod is installed. The surgeon then manipulates the template 70' to a desired shape in operation 616. This includes the surgeon performing any further manipulation of the patient and vertebra to a desired position as may be required. In this application of the present method it is understood that the template 70' is formed to have a high degree of plasticity or be flaccid. As used herein, the term "flaccid" means the template 70' conforms under its own weight to resting on the pedicle screws. In other words, the surgeon need only lay the template 70' on the engagement portions of the pedicle screws. Alternatively, the template 70' may have a yield strength of 0.05 lbs-ft or higher which permits the surgeon to manually conform the template 70' to a desired shape with little force while in place on the pedicle screws with the template 70' either maintaining the shape upon removal or not maintaining the shape as data has already been obtained. A data storing operation 618 is then conducted wherein the interrogator 60 is polled for shape data of the template 70' placed in-situ and the shape data is stored in the controller 40. The template 70' is then removed from the interrogator 60 in operation 620. In this data acquisition operation 502*b*, since the template 70' is placed in-situ when measurements are taken, retention of shape of the template 70' is not required. Thus, it is also possible that instead of the template 70', the actual fiber optic shape sensor 62 may be used.

Figure 8C:
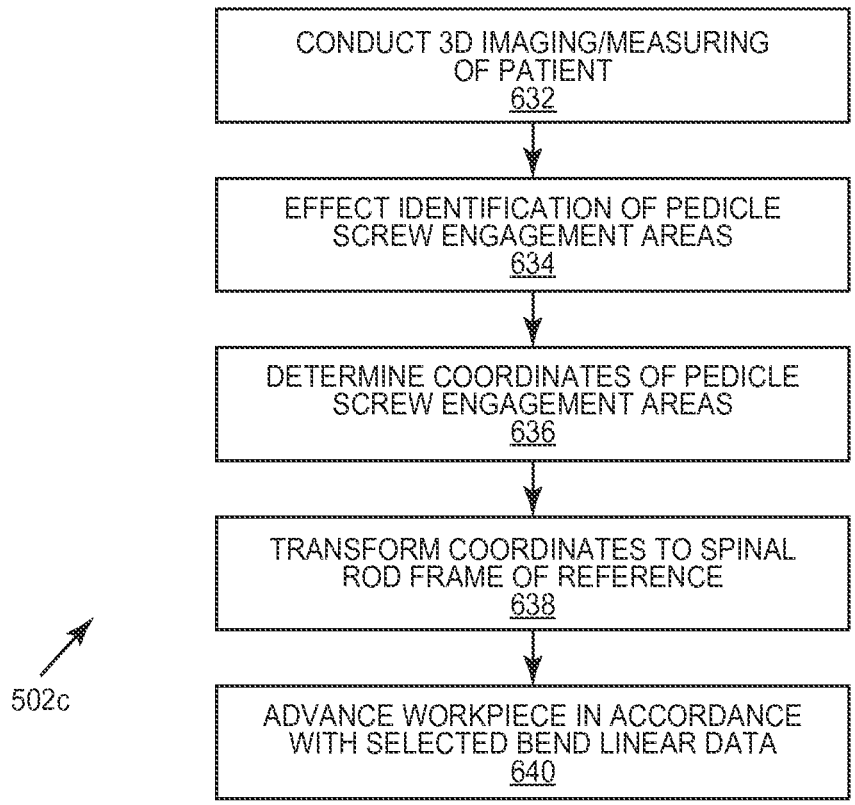
FIG. 8c is a flowchart of a third embodiment of a data acquisition operation of the forming method of FIG. 7 entailing imaging or mechanical data acquisition.

Referring to FIG. 8*c*, the data acquisition operation 502 is optionally embodied as a third data acquisition operation 502*c*. The third embodiment of the data acquisition operation 502*c* includes performing 3D measuring by mechanical contact or imaging in a data acquisition operation 632. The data acquisition operation 632 may be conducted using an articulated mechanical measuring device having one or more feeler devices for measuring individual positions of pedicle screw engagement areas, or other targets, by mechanical contact using digital encoders such as, for example and not limitation, in U.S. Pat. No. 8,177,843. Other mechanical contact systems may be employed as are known in the art for measuring points on an object in 3D space such as those used for verifying dimensions of manufactured components. The relative coordinates of measurement points of the one or more feeler devices, which is/are placed on the engagement areas of the pedicle screws, or other targets, are thus obtained. Alternatively, this operation may be effected using 3D imaging via x-rays, or optical techniques. An identification operation 634 comprises identifying the engagement areas of the pedicle screws, or other targets, in the 3D images capture the coordinates thereof. A transformation operation 638 next transforms the coordinate data to the frame of reference of the spinal template 70. Finally, the transformed coordinate data is stored for later use by the bender 64. Alternatively, the transformation operation 638 may be omitted and the actual coordinate data, obtained via either the mechanical measuring or imaging, may be stored and later transformed when used to operate the bender 64.

The data acquisition operation 502 may produce substantially continuous data as in the case of the first and second data acquisition operations, 502*a* and 502*b*, which employ the template 70', or discrete data as in the case of the third data acquisition operation 502*c*. For the purpose of this disclosure, "substantially continuous data" is intended to mean a set of data which includes coordinate data representative of positions taken along defined increments of the template 70', or other measuring device, such as every tenth of an inch or other predefined interval down to the resolution of the measuring device employed, which are outside the immediate vicinity of the targets, e.g., pedicle screw engagement areas. "Discrete data" means data taken at points of engagement of the workpiece, e.g., the spinal rod 70, with the targets, e.g., pedicle screws, which identify positions of the workpiece which are required for functioning of the workpiece.

Figure 9:
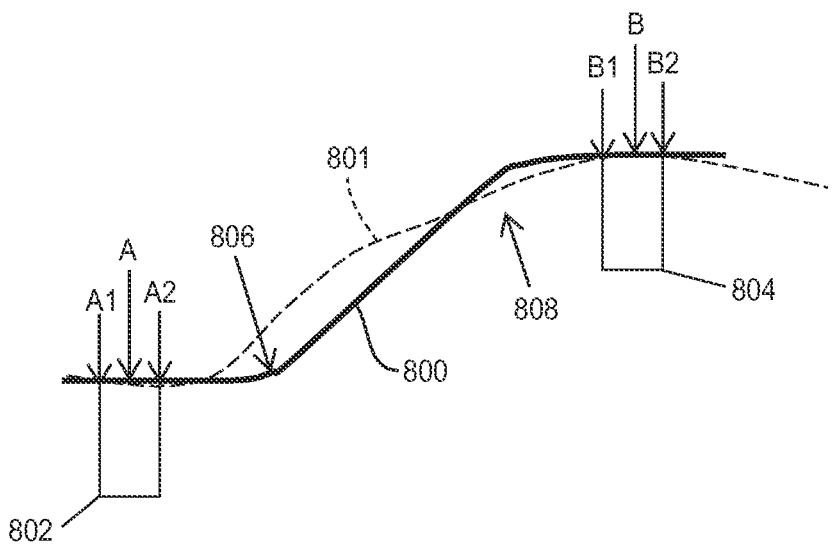
FIG. 9 is a graphic depiction of bending of a workpiece and acquired data.

Operation of the bender 64 includes translation of the shape data into bender control data which directs operation of actuators, e.g., motors, of the bender 64. The bender control data includes bend linear data, bend plane angle data, and bend angle data which respectively dictate where bends are made along the length of the workpiece, an angle at which the workpiece is oriented during a bend which determines the plane angle, relative to a reference angle of the workpiece, and thus the radial plane of the workpiece in which a bend made, and an amount of bend to be made. In the case of discrete data, calculation of the bender control data includes determining the bends to be made between target positions on the workpiece which are to engage the targets. Referring to FIG. 9, first and second targets, 802 and 804, will have a workpiece 800, e.g., a spinal rod 70 in the case of the example of this disclosure, attached to them as shown. For discrete data, the coordinates of points A and B are taken and the controller 40 or bender 64 includes a bend determination program which calculates the bender control data for effecting bends 806 and 808 based on the coordinates of points A and B.

Various methodologies may be employed for calculating the bender control data but generally the methods will minimize the number of bends between target points and calculate bends within the limitations of the bender 64. For example, the bend determination program can accept target coordinates A and B and determine that a given amount of straight lengths about the targets are to be maintained and that bends are to begin at the terminations of those straight lengths. Thus, assuming that no two targets are on a same straight line, and that all target lengths are parallel one another, two bends will be made in the workpiece between each adjacent target pair. In the case where all target lengths are not parallel, two spaced apart target defining coordinates may be taken for each point A and B, for example at the ends of each target block, 802 and 804, illustrated as A1, A2, B1, and B2, which will determine the orientation of the straight length at the target. In either case, for bending at the terminations of the straight lengths, bend data is calculated to join the adjacent straight lengths on the workpiece by appropriately bending the workpiece. It is understood that although FIG. 9 presents a two dimensional representation of bends, the above explanation also applies to bends made in three dimensions wherein targets are not coplanar.

When the template 70' is used, the fiber optic shape sensor 62 will produce substantially continuous data as illustrated by curve 801 in FIG. 9. The surgeon forming the template will not necessarily make exact bends and will possibly form curvatures that are more continuous than discrete so as to place the workpiece at targets for engagement. Accordingly, the bend determination program may function in any of several ways.

A first bending method, curve fit bending, calculates a series of incremental bends which form the workpiece to closely match the shape data represented by curve 801. Such curve fit bending is optionally characterized by an increment length which dictates discrete positions at which bends are made along the workpiece. Such increment lengths may vary, for example and not limitation, from 0.1" to 2" or more depending on bender limitations and the application. Smaller increments are feasible for small workpieces and appropriately constructed benders. For the purpose of this disclosure, such bending will be termed "curve fit bending" and will mean bending wherein more than two bends are made between target areas to conform the workpiece to the manually introduced bends of the template 70'. Curve fit bending may have limitations dictated by construction of the bender 64 which will manifest themselves in bend radius and bend spacing limitations, i.e., the increment lengths.

A second bending method is a minimum bend method which is illustrated by the workpiece 800 in FIG. 9. Given target positions A and B and associated target defining coordinates A1, A2, B1, and B2, the minimum bend method mathematically determines two bends, 806 and 808, necessary for forming the workpiece 80 to make proper engagement at the targets A and B. Positions of the target defining coordinates A1, A2, B1, and B2, along the template 70' may be input for each target A and B or, alternatively, a predetermined target length about each target A and B may be input and used to identify the target defining coordinates A1, A2, B1, and B2. The predetermined target length may be the same for all targets A and B, or may be more than one predetermined target length with the lengths varying from target to target. The calculations necessary for defining the bends are readily determined by those of ordinary skill in mathematics in light of this disclosure and details thereof are hence omitted.

For the minimum bend method, target coordinates of targets A and B, and optionally the associated target defining coordinates A1, A2, B1, and B2, along the length of the template 70' may be identified in any one of several ways. The term "shape data" as used in this disclosure is intended to mean coordinate data indicating the shape of the template 70' as indicated by the fiber optic shape sensor 62 and, optionally as needed, the target coordinates and, if a predetermined target length is not used, the target defining coordinates A1, A2, B1, and B2 first identification method utilizes a scale incorporated into the template 70' which will permit input of positions along the template 70', i.e., linear identifier coordinates, which correspond to targets A and B, and optionally the associated target defining coordinates A1, A2, B1, and B2, if used, via the computer 50 and keyboard 54. Other manual input methods such as touch screen or voice may optionally be used. A second identification method includes the template 70' having a touch sensing capability such that a user touches the template 70' at positions of targets A and B, and optionally the associated target defining coordinates A1, A2, B1, and B2, and cues the controller 40 to accept a coordinate of the touch on the template 70' as a target position or an associated target defining coordinate. The touch sensing capability may either be inherent in the fiber optic shape sensor 62 or may be achieved by a touch sensitive strip 73, see FIG. 1, for example a linear touch sensor, optionally included in the template 70'. The controller 40 accepts linear identifier coordinates identifying target positions along the template 70', and said template includes a linear touch sensor for accepting contact as input of a position of the contact. Other techniques may be adapted to identifying positions along the template 70' and are considered to be within the scope and spirit of the present disclosure.

Figure 10:
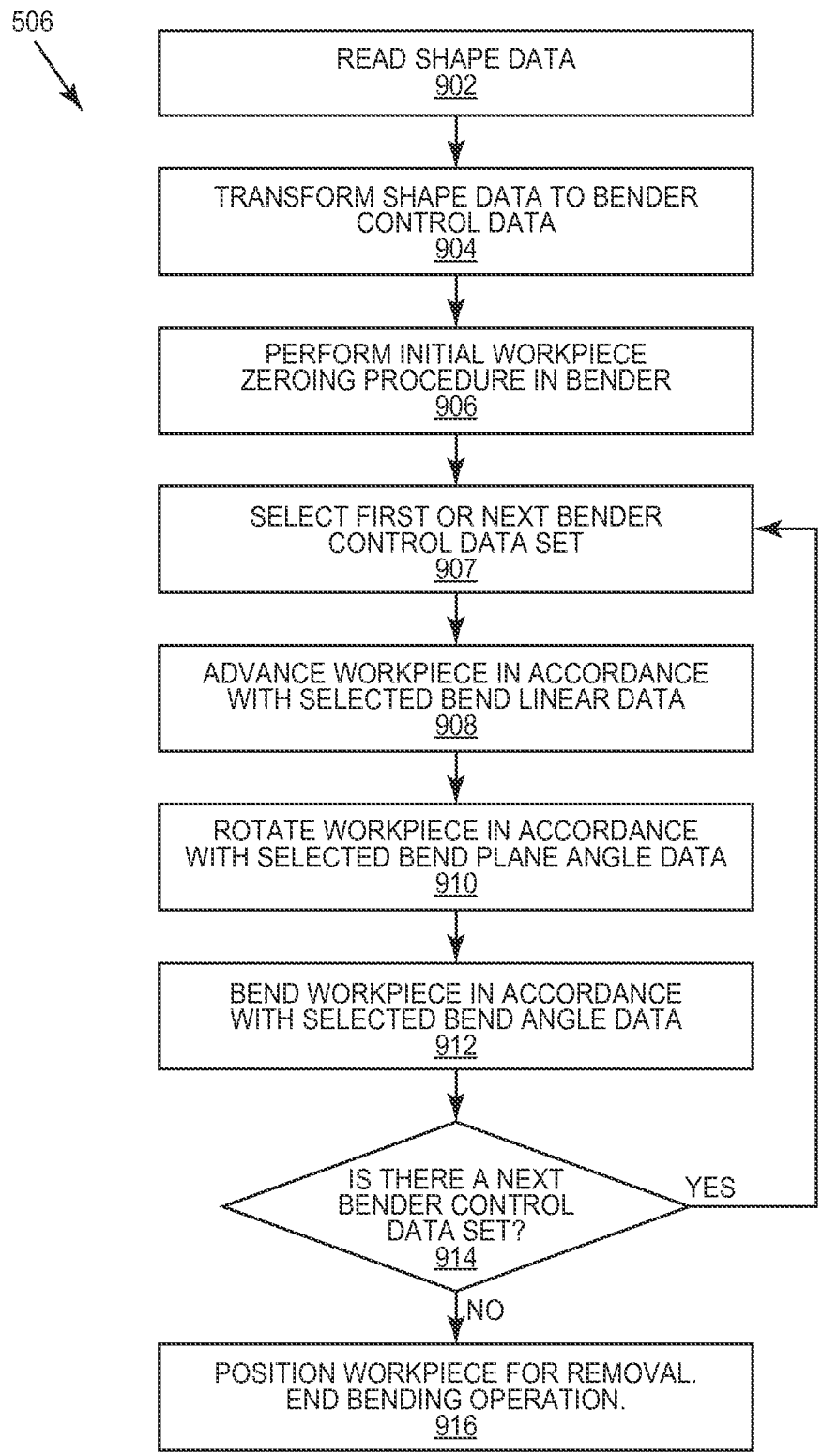
FIG. 10 is a flowchart of an embodiment of a bending operation effected by the bending apparatus of FIG. 1 in accordance with the forming method of FIG. 7.

The bender 64 uses the bender control data to effect bends in the workpiece. Referring to FIG. 10, the forming operation 506 includes a reading operation 902 in which the shape data previously stored is read and a transformation operation 904 in which the shape data is converted to bender control data. The bend linear data of the bender control data dictates where along the length of the workpiece a bend is made and is based on the increment lengths for the curve fit bending method, or the target coordinates and associated target defining coordinates, or predetermined target lengths, for the minimum bend method. Once the workpiece, for example the spinal rod 70, is mounted in the collet 94 with the fiber optic shape sensor 62 is disposed associated with the workpiece, a zeroing operation 906 is performed in which the workpiece is positioned via manual bender control or automated bender control so that an end of the workpiece is situated at an origin position and the bender 64 is calibrated to recognize this position as a zero position from which further operations of the bender 64 are calculated. In a selection operation 907, a first set of bender control data is selected for controlling the bender 64. In a linear positioning operation 908, the bender 64 is actuated in accordance with the linear bend data of the selected set of bender control data to relatively move the support assembly 90 and the bender assembly 95 to position the workpiece so that a bending operation will place a bend beginning at the position designated by the bend linear data, i.e., the position on the workpiece identified by the bend linear data is situated in contact with the mandrel member 98. The workpiece is then rotated by the stepper motor 91 in a rotation operation 910, if necessary, in accordance with the bend plane angle data for the particular bend so that a bend to be made will lie in the plane identified by the bend plane angle data. It is understood that the order of the operation for relative movement of the support assembly 90 and the bender assembly 95 and the operation of the stepper motor 91 for rotating the workpiece may be interchanged. Once correctly positioned for a bend to be made, the bend is made by a bending operation 912 advancing the bending member 98 to bend the workpiece about the mandrel member 96 in accordance with the bend angle data. Once the bending operation 912 is completed, a decision operation 914 determines if there are further bends to be made. If the determination is positive, control then proceeds back to the selection operation wherein a next set of bender control data is selected for operating the bender 64. If the determination is in the negative, flow proceeds to the removal operation 916 wherein the workpiece is positioned for removal from the collet 94.

Figure 11:
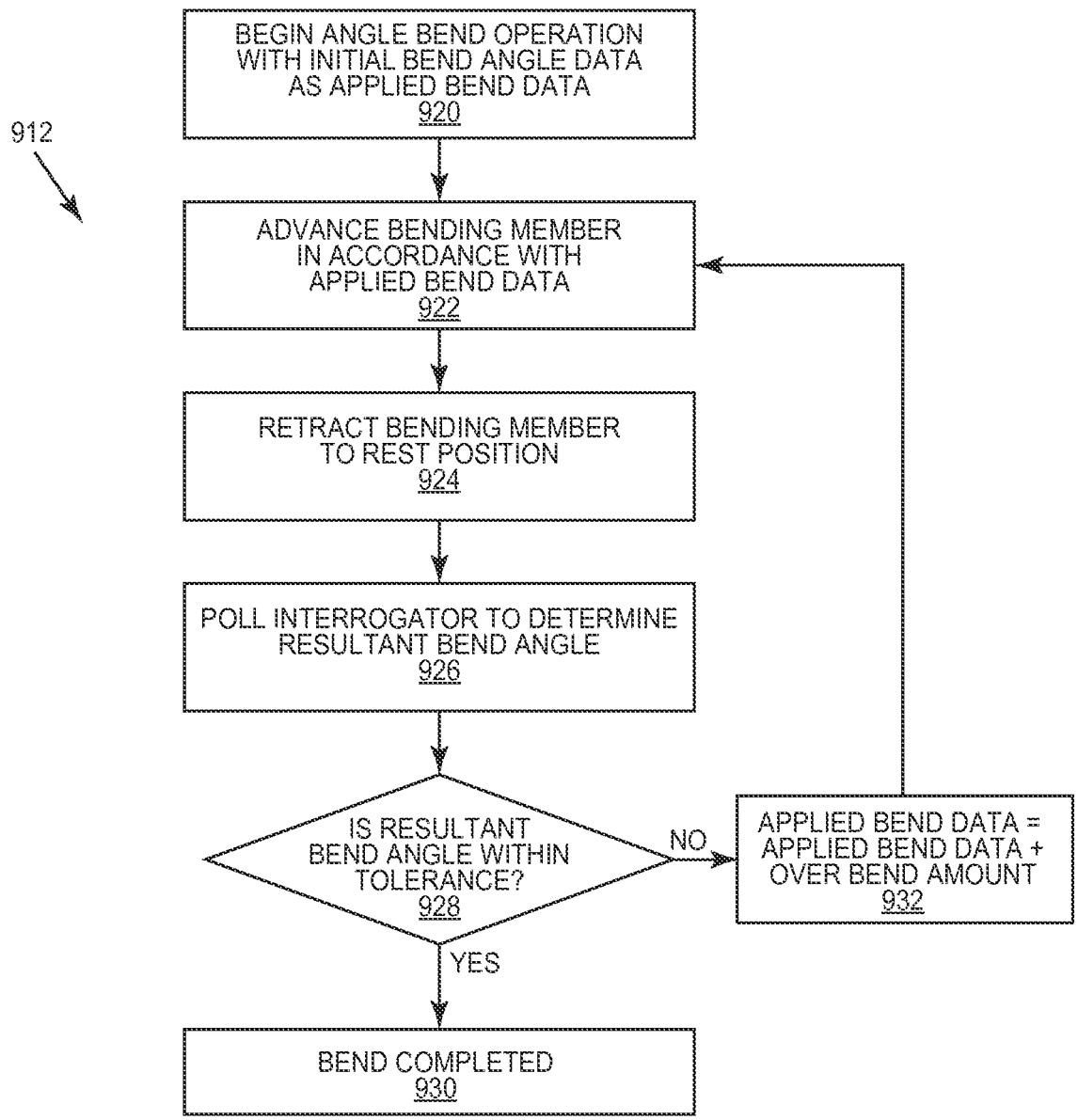
FIG. 11 is a flowchart of an embodiment of an angle bending operation effected by the bending apparatus of FIG. 1 in accordance with the bending operation of FIG. 10.

As previously discussed, bending the workpiece will result in spring back, or elastic strain being released, when the bending member 98 is retracted to its initial rest position. Thus, although the bending member 98 is advanced to a position where the workpiece is bent M number of degrees with the bending member 98 applying force Fz to the workpiece, when the bending member 98 is retracted, spring back will occur so that the workpiece springs back to a position of N number of degrees less than M which is representative of the elastic strain experienced by the workpiece. Therefore, to achieve a permanent bend of M degrees, the bending member 98 must be advanced an amount S greater than that for a force applied bend of M degrees. As previously noted, the amount of spring back is not always well defined so it is difficult to predict the amount of S to compensate for the spring back. Therefore, referring to FIG. 11, the bending operation 912 starts with the bend angle data of the selected bender control data set being used as applied bend data. A bending member advance operation 922 actuates the bending member 98 to move to a position where the workpiece is bent the amount dictated by the applied bend data. Next, a retraction operation 924 retracts the bending member 98 to a position whereat no force is applied by the bending member 98 to the workpiece or the bending member 98 is disengaged from the workpiece. This allows spring back to occur. A polling operation 926 is then performed wherein an angle of a resultant bend effected is determined from reading the fiber optic shape sensor 62 via the controller 40 and interrogator 60. A decision operation 928 next compares the resultant bend with the bend angle data to determine if it is within tolerance. If it is not in tolerance, then spring back must be corrected for and a new applied bend angle data is determined in angle adjustment operation 932 that will bend the workpiece a greater amount than the prior bend operation. In other words, an over bend amount is added to the applied bend data to produce new applied bend data. The over bend amount may be a preset amount, such as 10% of the initial bend, or five degrees, or another preset amount that is selected based on the material of the workpiece which is stored in memory and selected or directly input to the controller 40.

Alternatively, an amount is optionally determined by the computer based on prior bends of the material of the workpiece for which the applied force bend amount M is stored along with a resultant bend amount in a look-up table, for each of a range of applied bend amount M. Use of such a look-up table includes finding a resultant bend amount needed and operating the bender 64 to effect the bend amount M associated with the resultant bend amount to achieve a desired bend. It is understood that interpolation is optionally employed for bend amounts not explicitly included in the look-up table.

The look-up table is optionally created as part of a calibration procedure executed on a sample workpiece prior to operations being conducted on the actual workpiece. Since materials vary from lot to lot, optionally the sample workpiece is selected from the same lot as the actual workpiece. Alternatively, a look-up table is created for a given material and used regardless of lot variations. Another option is that either a look-up table or a mathematically calculated over bend is determined from predefined data material characteristics data defining the stress-strain characteristics of the material, as shown in the exemplary graph of FIG. 6, or other material defining measure. In some embodiments, the look-up table or mathematical formulas are stored in the controller 40. A still further option is that the bender 64 be configured to measure applied force and, with input from the fiber optic shape sensor 62, effect real-time stiffness measurements of a force displacement curve to detect the elastic/plastic transition to determine an amount of over bend needed to effect a desired final bend.

In still another alternative compensation method, the over bend amount may be set to the difference between the measured bend and that required by the initial bend data and may be added to applied bend data used to operate the bender in the next bending operation. Optionally, the over bend amount is selected to be somewhat less than what may actually be required to prevent the occurrence that the workpiece is permanently bent an amount greater than the requirement of the bend data.

Operation flow then proceeds back to the bending member advance operation 922 wherein the new applied bend data is used. If the decision operation is affirmative, i.e., the effected bend produces a resultant measured bend within a predetermined tolerance amount of the bend data then the bend is completed and flow proceeds to operation 930 which returns flow to the forming operation of FIG. 10.

In some embodiments, in the above discussion, the fiber optic shape sensor 62 is used to detect the shape of the workpiece and the template 70'. However, it will be understood by those skilled in the art that the fiber optic shape sensor 62 operates on optical principles used to detect strain in optical fibers from which a shape of the fiber is extrapolated, and that, alternatively, an embodiment employing one or more of strain gauges, optical strain mapping, or optical curvature measurements may be used in place of the fiber optic shape sensor 62.

In summary, if the effected bend is less than needed to be within the predetermined tolerance amount of the bend data, a newly determined over bend amount will be added to the applied bend data and another bend made in the workpiece until the resultant measured bend is within the predetermined tolerance amount of the bend data. Following completion of the bend to within the predetermined tolerance amount of the bend data, the bender operation is controlled to again linearly position the workpiece for a next bend and the operation is repeated. The use of the fiber optic shape sensor 62 allows the workpiece to be measured while clamped in the bender 64 and thus bending to accomplished which corrects for spring back. Depending on the construction of the template 70', the fiber optic shape sensor 62 employed in the template 70' is optionally removed from the template 70' and incorporated into the workpiece, i.e., the spinal rod 70 for executing the forming method 500. Alternatively, a second fiber optic shape sensor 62 is used for the workpiece.

It is to be understood that the apparatus and method of the present disclosure optionally includes an embodiment operating the bender 64 using an iterative operation wherein once a bend is made, it is measured and further bending is effected until the resultant bend is within tolerance. Alternatively, the apparatus and method of the present disclosure optionally includes an embodiment wherein a material characteristic data calculated bend amount is determined based on any of, material characteristic data corresponding to a material type of a workpiece, or material characteristic data corresponding to a sample material of a workpiece. The material characteristic data is optionally in the form of a look-up table or numerical values corresponding to variables, coefficients, or constants used in a formula or formulas for determining a resultant bend amount.

It will be apparent to those skilled in the art that various modifications and variations can be made to various embodiments described herein without departing from the spirit or scope of the teachings herein. Thus, it is intended that various embodiments cover other modifications and variations of various embodiments within the scope of the present teachings.

What is claimed is:

1. A forming apparatus for forming a workpiece for use in a medical procedure wherein the workpiece is to be fitted to a patient by bending, comprising:
   a bending machine comprising a shaft defining an axis, the shaft being connected to a motor, the workpiece being coupled to the shaft such that motor rotates the workpiece about the axis;
   a fiber optic shape sensor which is manually formable, said forming apparatus being configured to sense a shape of the shape sensor such that a relative position of at least two portions of the shape sensor relative to each other are measurable, wherein said shape sensor is disposed in a sensor channel of the workpiece; and
   a controller configured to receive template shape data from said shape sensor and operate said bending machine to effect bending of the workpiece in accordance with the template shape data, wherein said bending of said workpiece includes a spring back compensating operation comprising one of an iterative bending operation or a material characteristic data calculated bend amount.

2. A forming apparatus according to claim 1, wherein said spring back compensating operation is an iterative bending operation comprising:
   performing a first bending operation on said workpiece in accordance with said template shape data;

acquiring workpiece shape data from said shape sensor so as to provide workpiece shape data, representative of said workpiece, to said controller; and performing a second bending operation compensating for spring back due to elastic deformation during said first bending operation based on said template shape data and said workpiece shape data.

3. A forming apparatus according to claim 2, wherein the sensor channel is a bore.

4. A forming apparatus according to claim 1, wherein:
said controller is configured to accept linear identifier coordinates identifying target positions along the shape sensor;
said shape sensor includes indicia identifying linear positions along said shape sensor; and
said controller is configured to effect minimum bend bending via said bender wherein a number of bends, between the target positions, are minimized and bends are affected outside of defined areas including said target positions.

5. A forming apparatus according to claim 4, wherein said controller is configured to accept linear identifier coordinates identifying said defined areas.

6. A forming apparatus according to claim 1, wherein:
said shape sensor includes a linear touch sensor for accepting contact at a position to effect input of coordinates of the position of the contact;
said controller is configured to accept input from said linear touch sensor as linear identifier coordinates identifying target positions along the shape sensor; and
said controller is configured to effect minimum bend bending via said bender wherein a number of bends, between the target positions, are minimized and bends are affected outside of defined areas including said target positions.

7. A forming apparatus according to claim 6, wherein said controller is configured to accept input from said linear touch sensor as linear identifier coordinates identifying said defined areas.

8. A forming apparatus according to claim 1, further comprising an interrogator that is connected to the shape sensor, the interrogator being configured to analyze reflections from a laser signal applied to the shape sensor using optical frequency domain reflectometry to determine a shape imposed on the shape sensor when the laser signal is applied to the shape sensor.

9. A forming apparatus according to claim 1, wherein the fiber optic shape sensor comprises optical fiber cores.

10. A forming apparatus for forming a spinal rod, the apparatus comprising:
a bending machine comprising a shaft defining an axis, the shaft being connected to a motor, the spinal rod being positioned between a mandrel member of the bending machine and a bending member of the bending machine, the spinal rod being coupled to the shaft such that motor rotates the spinal rod about the axis;
a fiber optic shape sensor which is manually formable, the shape sensor being positioned in a sensor channel of the spinal rod;
an interrogator that is connected to the shape sensor, the interrogator being configured to analyze reflections from a laser signal applied to the shape sensor using optical frequency domain reflectometry to determine a shape imposed on the shape sensor when the laser signal is applied to the shape sensor; and a controller configured to receive template shape data from the shape sensor and operate the bending machine to effect bending of the spinal rod in accordance with the template shape data.

11. A forming apparatus for forming a workpiece, the forming apparatus comprising:
a bending machine comprising a shaft defining an axis, the shaft being connected to a motor, the workpiece being coupled to the shaft such that motor rotates the workpiece about the axis;
a fiber optic shape sensor disposed in a sensor channel of the workpiece;
an interrogator configured to sense a shape of the shape sensor; and
a controller configured to receive data regarding the shape of the shape sensor from the interrogator and operate the bending machine to effect bending of the workpiece in accordance with the data.

12. A forming apparatus according to claim 11, wherein bending of the workpiece includes a spring back compensating operation comprising a material characteristic data calculated bend amount.

13. A method for forming a workpiece for use in a medical procedure wherein the workpiece is to be fitted to a patient by bending, comprising:
providing said forming apparatus of claim 1;
manually shaping said shape sensor to fit the patient; and
operating said controller to effect bending of said workpiece based on said template shape data using said spring back compensating operation.

14. A method for forming a workpiece for use in a medical procedure wherein the workpiece is to be fitted to a patient by bending, comprising:
providing said forming apparatus of claim 1;
manually shaping said shape sensor to fit the patient by placing said shape sensor in-situ;
positioning the shape sensor in the sensor channel; and
operating said controller to effect bending of said workpiece based on said template shape data using said spring back compensating operation.

15. A method according to claim 14 wherein said shape sensor is limp and said manually forming comprises laying said shape sensor in-situ and acquiring said template shape data with said shape sensor laying in-situ.

16. A method according to claim 15, wherein said workpiece is a spinal rod.

17. A method for forming a workpiece for use in a medical procedure wherein the workpiece is to be fitted to a patient by bending, comprising:
providing said forming apparatus of claim 4;
manually shaping said shape sensor to fit the patient;
inputting linear identifier coordinates of at least one of said target positions or said defined areas;
positioning the shape sensor in the sensor channel; and
operating said controller to effect said minimum bend bending of said workpiece based on said template shape data, and said linear identifier coordinates of at least one of said target positions or said defined areas, using said spring back compensating operation.

18. A method according to claim 17, wherein said workpiece is a spinal rod.

19. A method for forming a workpiece for use in a medical procedure wherein the workpiece is to be fitted to a patient by bending, comprising:
providing said forming apparatus of claim 4;
manually shaping said shape sensor to fit the patient by placing said shape sensor in-situ;

inputting linear identifier coordinates of at least one of said target positions or said defined areas;

positioning the shape sensor in the sensor channel; and operating said controller to effect said minimum bend bending of said workpiece based on said template shape data, and said linear identifier coordinates of at least one of said target positions or said defined areas, using said spring back compensating operation.

20. A method according to claim 19 wherein said shape sensor is limp and said manually forming comprises laying said shape sensor in-situ and acquiring said template shape data with said shape sensor laying in-situ.

* * * * *